United States Patent [19]

Eidenbenz et al.

[11] Patent Number: 5,244,933
[45] Date of Patent: Sep. 14, 1993

[54] DENTAL COMPOSITIONS WHICH CAN BE PREPARED AND WORKED BY THE ACTION OF OSCILLATIONS AND METHOD FOR THE PREPARATION THEREOF

[75] Inventors: Stefan Eidenbenz, Zürich, Switzerland; Klaus Ellrich, Wörthsee, Fed. Rep. of Germany; Oswald Gasser, Seefeld, Fed. Rep. of Germany; Rainer Guggenberger, Herrsching, Fed. Rep. of Germany; Andreas Iburg, Wörthsee, Fed. Rep. of Germany; Peter Koran, Weilheim, Fed. Rep. of Germany; Michael J. Noack, Berlin, Fed. Rep. of Germany; Reinhold Nowak, Adelshofen, Fed. Rep. of Germany; Francois Roulet, Berlin, Fed. Rep. of Germany; Klaus-Peter Stefan, Seefeld, Fed. Rep. of Germany; Werner Zöllner, Oberpfaffenhofen, Fed. Rep. of Germany

[73] Assignee: Thera Patent GmbH & Co. KG Gesellschaft für industrielle Schutzrechte, Seefeld, Fed. Rep. of Germany

[21] Appl. No.: 775,314

[22] Filed: Oct. 11, 1991

[30] Foreign Application Priority Data

Oct. 12, 1990 [DE] Fed. Rep. of Germany ....... 4032505
Feb. 18, 1991 [DE] Fed. Rep. of Germany ....... 4104934

[51] Int. Cl.$^5$ .......................... A61K 6/08; A61C 5/00; C08K 9/06; C08F 2/48
[52] U.S. Cl. .......................... 522/3; 522/77; 522/182; 522/908; 522/79; 522/81; 523/116; 433/228.1; 106/35
[58] Field of Search .......................... 522/3, 908, 77, 79, 522/182, 3, 908, 81; 523/116; 433/228.1; 106/35

[56] References Cited

U.S. PATENT DOCUMENTS

| 3,825,518 | 7/1974 | Foster et al. | 260/42.52 |
| 3,862,920 | 1/1975 | Foster et al. | 260/42.52 |
| 4,114,271 | 9/1978 | Howa | 427/2 |
| 4,131,729 | 12/1978 | Schmitt et al. | 526/282 |
| 4,219,619 | 8/1980 | Zarow | 433/118 |
| 4,459,193 | 7/1984 | Ratcliffe et al. | 522/908 |
| 4,610,631 | 9/1986 | Beyer et al. | 523/116 |
| 4,674,661 | 6/1987 | Heroid | 222/386 |
| 4,767,798 | 8/1988 | Gasser et al. | 523/117 |
| 4,850,875 | 7/1989 | Takatsu | 433/226 |

FOREIGN PATENT DOCUMENTS

| 765627 | 4/1971 | Belgium . |
| 232733 | 8/1987 | European Pat. Off. . |
| 3611990 | 10/1987 | Fed. Rep. of Germany . |

Primary Examiner—Susan Berman
Attorney, Agent, or Firm—Robert W. Becker

[57] ABSTRACT

Curable compositions are described which contain a binder and a high proportion of fillers having a mean grain size of <50 μm. The filler proportion of the curable compositions is so high that they cannot be used for the intended purpose because of their high viscosity However, they can be liquefied by exposure to oscillation in the frequency range of 20 Hz to 20 MHz with an amplitude of 1 μm to 5 mm so that they are workable and can be employed for the intended purpose.

37 Claims, No Drawings

DENTAL COMPOSITIONS WHICH CAN BE PREPARED AND WORKED BY THE ACTION OF OSCILLATIONS AND METHOD FOR THE PREPARATION THEREOF

DESCRIPTION

The invention relates to dental compositions which can be made and worked by the action of oscillations and a method for the preparation thereof as well as the use of highly filled dental filling materials (filling composites) for cementing inlays, onlays, veneers and the like by means of high-frequency vibrations. Such compositions include in particular dental preparations, for example filling compositions, but also other compositions, such as adhesives and fillers.

In many technical fields, for example in the field of dental compositions and adhesive compositions and fillers, highly filled viscous curable compositions are used to fill defects or join defective parts together. The durability of these restorations is governed essentially by the properties of the binders and fillers, the binders generally representing the weaker part. It has therefore been found that the compositions permit particularly durable and high-quality restorations whenever the filler content is very high. Thus, in dentistry, dental filling compositions having up to 85% by weight fillers are offered and dental cements usually have 50 to 60% by weight fillers.

This incorporation of fillers is limited in particular by the viscosity setting which the user requires. Thus, for example, dental filling compositions must still be plastically formable enough for the dentist to be able to introduce them with suitable instruments, for example spatulas and ball point pluggers, into the cavity, for them to be liquefiable under pressure to such an extent that they can fill the cavity completely by flowing and for them to be still workable with the instruments in such a manner that the surface can be adapted to the natural situation. To mount inlays, onlays, veneers and the like, usually readily flowing cement compositions are used which as a rule have a low content of inorganic fillers. Such cement compositions harden either by ion reactions, for example socalled zinc phosphate or glass ionomer cements, or by polymerisation reactions, for example by radical polymerisation of methacrylic acid esters.

These latter materials are used in particular when adequately transparent inlays, onlays and veneers are involved, for example of porcelain or resin. The standard materials preferably used for this purpose are photocurable materials, and in some cases an aftercuring is effected with a following redox process.

European patent 0 325 266 describes for example dental materials which may also be used for cementing inlays, onlays and veneers and which are cured in two steps. For this purpose the compositions contain two different photoinitiators with different light absorptions. Although in this patent specification highly filled dental filling compositions are described, cement compositions which are made by this system usually have less than 50% by weight fillers.

The demands in the field of cementing materials and adhesives are even more stringent. Since here it is frequently necessary to fill minute gaps with the adhesives, elevated flowability under pressure is necessary. Usually, here film thicknesses $<25$ $\mu$m should be obtainable under low pressure.

It was therefore hitherto not possible to prepare and use compositions which are so highly viscous and are thus filled with filling bodies to such an extent that they can still be acceptably employed by the user.

Conventionally, most multicomponent preparations are mixed with a spatula on a support, for example a block. Thus, suitable volumes or volumes of the individual components predosed in the mixing ratio are placed on a block and subsequently mixed with a spatula. However, this procedure works hitherto only with relatively low viscosity or highly thixotropic materials which become liquefied by the mixing movement to such an extent that complete mixing is thereby ensured. With less thixotropic and very highly filled materials it is not possible to apply these shearing forces at all.

It is further known to mix predosed multicomponent materials in capsules (e.g. EP 0 157 121). As a rule, this is a powder/liquid system, the powder, for example a glass ionomer cement powder, being stored in the capsule interior, and a liquid component which is injected by a special activator system before the mixing being stored in a pad attached outwardly to said container. These capsules are thereafter mixed under high-frequency oscillations with amplitudes $>5$ mm in the capsule. The disadvantage of this system is however that the energy transfer is relatively poor and that in the mixing movements in the chamber a certain amount of air is frequently introduced as well.

It is known from EP 0 232 733 to mix low-viscosity or medium-viscosity compositions (dental impression compositions or epoxy adhesives) homogeneously together by means of so-called static mixing elements. In this case the materials are pressed through a cannula into which a mixing spiral is inserted. U.S. Pat. No. 4,219,619 describes a vibrating dental instrument for inserting crowns and bridges. By relatively low-frequency vibration in the range of 20–100 Hz, in this case a usual low-viscosity cement is liquefied on inserting the crown by means of the transfer chain vibrator/bite registration/crown. Liquefication of high-viscosity compositions is not described here. The use of filling composites or composite cements is not described either. Moreover, the method requires a specific instrument which must be specially acquired by the dentist.

Thus, hitherto no method was available with which multicomponent highly filled highly viscous compositions could be mixed uniformly at the user's (i.e. by hand or in a mixing capsule).

The objective of the invention is to solve the aforementioned problems by making available to the user extremely highly filled and highly viscous compositions which can be prepared with novel preparation methods and can be applied with novel processes.

The essence of the invention is to be seen in that highly filled compositions, the viscosity of which is so high that they do not permit working with the usual methods, are liquefied by a vibration treatment so that they can be prepared, worked and employed in accordance with their purpose.

The subject of the invention is curable compositions which contain a binder and a high proportion of fillers having a mean (weight average) grain size of $<50$ $\mu$m and are characterized in that their filler proportion is so high that they cannot be used for the intended purpose because of their high viscosity and that by the action of an oscillation in the frequency range of 20 Hz to 20 MHz with an amplitude of 1 $\mu$m to 5 mm they can be liquefied so that they may be employed for the intended purpose.

The subject of the invention is further a method for preparing the aforementioned compositions which is characterized in that the fillers are mixed with the binder under the action of an oscillation in the frequency range of 20 Hz to 20 MHz with an amplitude of 1 μm to 5 mm.

The subject of the invention is further a method for mixing multicomponent highly filled highly viscous compositions, the components being mixed between two workpieces by shearing movements, the method being characterized in that at least one of the workpieces is set into oscillation in the frequency range of 20 Hz to 20 MHz with an amplitude of 1 μm to 5 mm.

The subject of the invention is further the use of highly filled dental filling materials for cementing inlays, onlays, veneers or the like by means of high-frequency vibrations.

The vibration is preferably generated by means of an ultrasonic device.

The frequency range according to the invention is preferably 50 Hz to 50 kHz and in particular 100 Hz to 30 kHz. The preferred amplitudes are 20 μm to 2 mm and in particular 50 μm to 1 mm.

With the method according to the invention it is also possible for the first time to mix compositions having a viscosity which is so high that said compositions could not be mixed with known methods by the user (that is by hand or in a mixing capsule). Such compositions in multicomponent form are advantageous in particular whenever several different curing mechanisms are to be combined with each other. It is particularly advantageous in the field of photocuring in shaded regions. In such cases a second curing mechanism independent of the illumination source can be incorporated, for example a redox initiator system for methacrylates. Said system consists for example of peroxides, such as benzoyl peroxide, and activators, for example amines, in particular aromatic amines or other reduction agents such as barbituric acids, or their derivatives, or alternatively malonyl sulfonamides and their derivatives.

For the dental compositions to be mixed according to the invention ethylenically unsaturated monomers or polymers may be used, for example monomeric and polymeric acrylates and methacrylates. In this connection attention is drawn to the compositions described in DE-OS 3,609,038, the X-ray-opaque fillers described therein possibly also being omitted.

As ethylenically unsaturated monomers or polymers for dental compositions, particular attention is drawn for example to the monomeric and polymeric acrylates and in particular methacrylates. In the case of polymerisable dental compositions, in particular the long-chain monomers of U.S. Pat. No. 3,066,122 on the basis of bisphenol A and glycidyl methacrylate are used, or the derivatives thereof obtained by addition of isocyanates. Also particularly suitable are the acrylic or methacrylic acid esters of monohydric or preferably polyhydric alcohols, for example triethylene glycol dimethacrylate and the like. Also particularly suitable are the diacrylic and dimethacrylic acid esters of bishydroxymethyl tricyclo-(5.2.1.0$^{2,6}$)-decane cited in DE-PS 2,816,823. It is also possible to use the reaction products of diisocyanates and hydroxyalkyl(meth)acrylates, as described for example in DE-OS 2,312,559. Of course, mixtures of suitable monomers or unsaturated polymers prepared therefrom may also be employed.

As photoinitiators, all substances may be used which after irradiation by UV or visible light initiate polymerisation, for example benzoinalkyl ethers, benzil ketals, acylphosphine oxides or aliphatic and aromatic 1,2-diketone compounds, for example camphor quinone, the photopolymerisation possibly being accelerated in a manner known per se by addition of activators, such as tertiary amines or organic phosphites.

Suitable initiator systems for initiating the polymerisation via a redox mechanism are for example the systems peroxide/amine or peroxide/barbituric acid derivatives and the like. When using such initiator systems, it is expedient to prepare an initiator (e.g. peroxide) and a catalyst component (e.g. amine) separately. The two components are then homogeneously mixed together just before use.

The method according to the invention can however also be advantageously employed for other multicomponent and high-viscosity compositions, such as for example for mixing high-viscosity impression compositions or dental cements, such as glass ionomer cements or zinc/phosphate cements.

A new field of application is also opened up by the use of highly filled high viscosity compositions which hitherto could not be reasonably mixed in the area of multicomponent adhesives and fillers.

However, methods of mixing dental preparations are preferred.

It has been surprisingly found that by the use of high-frequency vibrations in the mounting of inlays, onlays and veneers, even highly viscous, highly filled compositions become so readily flowable that the wetting of the replacement and the remaining hard tooth substance is optimum and very small film thicknesses of the cementing composite can be obtained.

High-frequency vibrations mean here vibrations of more than 200 Hz. Frequencies of more than 1 MHz are no longer suitable for the cementing.

Preferably, high-frequency vibrations of more than 1000 Hz, preferably more than 5000 Hz, particularly preferably more than 10000 Hz, are employed.

Expediently, the high frequency vibrations are applied for the cementing procedure with socalled "sonic scalers" and/or "ultrasonic scalers". Such devices have been in use for a long time in dental surgeries for removing tartar and filling excesses. When applying the ultrasonic vibrations, in addition a cooling is achieved simultaneously by supplying water. With the use according to the invention it is advantageous to turn off this water cooling and to act with the rounded scaler centre portion on the surface of the inlays, onlays or the veneers with low pressure so that said portion can sink into the cavity filled with composite.

It is advantageous here to arrange an intermediate layer, for example paper, waxed paper or the like, between the ultrasonic device and for example the inlay surface, in order to avoid any damage to the inlay surface by entrance of energy of the ultrasonic device. This can also be done in a favourable embodiment by placing a plastic sleeve over the scaler centre portion. The use of highly elastic rubber-like materials, for example bite impression materials, is not suitable for this purpose because said materials no longer transmit the high-frequency vibrations but absorb them.

The composite filling materials preferably contain the following components:

a) 60-95, preferably 70-90,% by weight inorganic fillers;

b) 4-39.99, preferably 9-29.9,% by weight ethylenically unsaturated polymerisable monomers and/or polymers;
c) 0 01-3, preferably 0.1-2,% by weight photoinitiators;
d) and possibly activators, initiators for the initiation of a redox polymerisation, as well as pigments, X-ray-opaque additives and/or thixotropy aids.

The filling bodies preferably have a mean particle-size distribution <20 μm and in particular <5 μm as well as an upper grain limit of 150, preferably 70 μm and in particular <25 μm. It is particularly advantageous to use socalled hybrid composites containing 5-25% by weight fillers with a mean grain size of 0.02-0.06 μm and 65-85% by weight fillers having a mean grain size of 1-5 μm. Inorganic fillers may for example be quartz, ground glasses, silica gels and pyrogenic silicic acids or their granulates. The at least partial use of X-ray-opaque fillers is particularly preferred. These may firstly be X-ray-opaque glasses, that is glasses containing for example strontium, barium or lanthanum, or alternatively part of the fillers consists of an X-ray-opaque additive, for example yttrium fluoride, strontium hexafluorozirconate or fluorides of the rare earth metals.

To improve the incorporation into the polymer matrix it is advantageous to hydrophobe the inorganic fillers. Usual hydrophobing agents are silanes, in particular trimethoxymethacryloyl oxypropylsilane.

The filler proportion in the compositions to be mixed may for example be 60 to 95% by weight, and for dental preparations filler proportions of 80 to 95% by weight and for adhesives and filling compositions 60 to 80% by weight are of particular interest.

To prepare the compositions according to the invention with high filler content, for example conventional kneading devices are employed to which an oscillation is applied in the frequency range of 20 Hz to 20 MHz with an amplitude of 1 μm to 5 mm. By the oscillation applied the components are kept liquid during the preparation procedure to such an extent that an appreciably increased filler content results. After stopping the oscillation the material is then of such high viscosity that it can no longer be worked with the usual techniques. It can then be worked only by again applying in accordance with the invention an oscillation in the frequency range of 20 Hz to 20 MHz with an amplitude of 1 μm to 5 mm.

With the method according to the invention for the mixing the procedure is such that the shearing between two workpieces is transmitted to the components. This may for example be done in that a vibrating spatula is employed and as counter piece a block or glass plate is again present. The material liquefies under the vibrating motions of for example the spatula and can be correspondingly well mixed. An alternative however is to use a vibrating spoon-like body in which with a usual commercial stationary spatula the materials can be mixed. A vibrating plate with a usual commercial spatula is another possible system. It is also possible to set both workpieces, i.e. for example spatula and block, in vibration simultaneously.

A further embodiment of the method according to the invention is the mixing in a dynamic or static mixer. The vibration can advantageously be applied either to the wall of the cannula or to the mixing spiral. It is possible then to mix together homogeneously even compositions which are so highly viscous that without vibration they cannot be pressed through said arrangement without destruction of the workpiece. This embodiment is particularly well suited to highly viscous dental impression compositions or adhesives or fillers.

To generate vibrations, either a separate device can be employed which is set into the corresponding vibration by means of piezoelectric or electromagnetic motors, or an insert can be made for an existing appliance used by the dentist, for example ultrasonic scaler or electrical toothbrush, which fits onto the corresponding counter pieces and after activation can in turn transfer the vibrations to the material. The generation of vibrations in the field of the invention is known in the art.

The advantages according to the invention are as follows:

1. Possible use for high-viscosity multicomponent cementing materials analogous to DE-OS 4,032,505 which can however now contain a second curing mechanism. This makes curing in shaded zones possible.

2. Air-bubble-free mixing is possible for the first time with multicomponent systems. With high-frequency vibrations in said range air bubbles may be completely removed from highly viscous materials. This positively influences the hardness of the material and in addition has the aesthetic advantage that the air bubbles would always be "visible" at the surface.

3. Preparation of dental compositions with very high filler content which in the cured state thus have a particularly high permanent strength and resistance to abrasion.

4. Minimizing of the polymerisation shrinkage, the thermal expansion and the abrasion by the increased filler proportion.

The invention will be explained in detail hereinafter with the aid of examples.

EXAMPLE 1

From 70 parts by weight bisacryloxymethyltricyclo-(5.2.1.0$^{2,6}$)-decane and 30 parts by weight 2,2-bis-4-(3-methacryloxy-2-hydroxypropoxyphenyl)-propane as well as one part by weight p-chlorobenzoyl peroxide, a homogeneous solution 1 is mixed.

With the same parts by weight monomer and 1 part by weight p-N,N-diethylaminotoluidine and 3 parts by weight N,N-dimethylaminoethyl methacrylate and 0.3 parts by weight camphor quinone a homogeneous solution 2 is mixed.

21 parts by weight of the solution 1 are kneaded with 55 parts by weight silanised tooth-dyed quartz having a mean grain size of 1.5 μm as well as 5 parts by weight silanised pyrogenic silicic acid having a mean grain size of 0.04 μm and 19 parts by weight silanised yttrium fluoride having a mean grain size of 1 μm to give a homogeneous paste 1 (catalyst paste).

21 parts by weight of the solution 2 are kneaded with the same parts by weight quartz, pyrogenic silicic acid and yttrium fluoride to give a homogeneous paste 2 (base paste).

Catalyst and base paste cannot be mixed together homogeneously using conventional means such as spatula/block, mixing capsules or the like.

0.5 g catalyst paste are placed with 0.5 g base paste into a spoon-like attachment for an electrical toothbrush. The material cannot be mixed with a commercially available plastic spatula and the viscosity is so high that even kneading no longer appears possible. After setting the electrical toothbrush into operation the spoon-like attachment oscillates with a frequency of 50 Hz and a deflection of 0.8 mm. In this condition the materials can instantaneously be mixed very easily and give a homogeneous mixed end product. Immediately after stopping the vibrations the mixed paste again has a high viscosity which makes it very easy to model the material.

The paste has a working time of 7 1/2 minutes and sets within 15 minutes (23° C.). The compressive strength of the hardened material after curing in darkness is 350 MPa and if the pressure-resistant body is also irradiated on both sides with a commercially available dental illumination unit (Elipar Visio, ESPE) for 20 sec., a compressive strength of 400 MPa is obtained. The surface hardness of the material is 240 MPa, after both dark curing and light curing.

The above example shows that it is possible for the first time with the method according to the invention to obtain a mixing of base and catalyst paste and thus to arrive at a material which has both the high viscosity properties and excellent physical properties after mixing with the method according to the invention. After the mixing the material is absolutely free of bubbles, i.e. the air bubbles usually also mixed into thinly liquid cements are completely eliminated by the vibration. The vibrations introduced cause the viscosity to decrease by about a factor of 10, as can be shown with the aid of a film thickness measurement. If about 500 mg base paste is introduced between 2 glass plates and the latter loaded thereafter with a total load weight of 15 kp, after a measuring time of 3 minutes a film thickness of 110 $\mu$m is obtained. If the measurement is carried out as above but the glass plates are set in vibration with the aid of the electrical toothbrush set forth in the example, a film thickness of 10 $\mu$m is obtained. This means that with the method according to the invention it is possible to employ for cementing purposes even pastes of such high strength that they normally have film thicknesses far above the required 25 $\mu$m. The vibrations introduced reduce the film thickness by the factor 10 from 110 $\mu$m to about 10 $\mu$m.

EXAMPLE 2

The two pastes of example 1 are placed in equal volumes on a commercially available mixing block (with surface of waxed paper). Thereafter, with a spatula attached to a commercially available ultrasonic device (Cavitron, Dentsply Company) said pastes are mixed together. After switching on the ultrasonic device (frequency about 28 KHz, amplitude 0.05 mm) the materials can be easily mixed together and after the mixing no air bubbles at all can be seen. After switching off the ultrasonic device the mixed paste again immediately has the original high viscosity. The materials thus mixed have physical properties as described in example 1.

EXAMPLE 3

A premixture is kneaded from 70 parts by weight bisacryloxymethyltricyclo-(5.2.1.2,6)-decane and 30 parts by weight 2,2-bis-4-(3-methacryloxy-2-hydroxypropoxy)phenyl propane (bis-GMA), 7 parts by weight silanised pyrogenic silicic acid, 0.3 parts by weight camphor quinone, 3 parts by weight N,N-dimethylaminomethyl methacrylate and 110 parts by weight yttrium fluoride as X-ray-opaque filler.

5.96 g of this premixture are kneaded with as great as possible an amount of silanised quartz (mean grain size about $\mu$m) pigmented to be similar to teeth. With a conventional planetary kneader, at the most 16 g filler can be kneaded in. However, if the kneader pot is placed on a vibrating plate oscillated with an amplitude of 0.5 mm and a frequency of 50 Hz, a further 6 g of the quartz can be kneaded in. Once the vibration has been switched off kneading is no longer possible and the material has a high viscosity and cannot be appreciably deformed under pressure.

If however this paste is taken up with a vibrating spatula as is described in example 2, the material can be introduced by the user into a cavity, again without any problems, and in this manner an extremely highly filled composite with an extremely low thermal expansion, extremely low abrasion and low polymerisation shrinkage is obtained. In addition, the material can be excellently worked with vibrating instruments, and the solid consistency after stopping the vibration is particularly advantageous, and consequently excesses and edges can be perfectly shaped in the nonpolymerised state.

EXAMPLE 4

A homogeneous solution is mixed from 70 parts by weight bisacryloxymethyltricyclo-(5.2.1.0$^{2,6}$)-decane and 30 parts by weight 2,2-bis-4-(3-methylacryloxy-2-hydroxypropoxyphenyl)propane, 0.3 parts by weight camphor quinone and 3 parts by weight N,N-dimethylaminoethyl methacrylate.

21 parts by weight of this solution are kneaded with 55 parts by weight silanised quartz dyed tooth colour having a mean particle-size distribution of 1.5 $\mu$m and 5 parts by weight silanised pyrogenic silicic acid having a mean particle-size distribution of 0.04 $\mu$m and 19 parts by weight silanised yttrium fluoride having a mean particle-size distribution of 1 $\mu$m to form a homogeneous paste. The paste has a highly viscous pasty consistency which "per se" is not suitable for cementing.

An inlay cavity is completely filled with the composite paste made in this manner. Thereafter, the prefabricated composite inlay (made from the same composite paste material but already completely cured throughout) is pressed into the cavity filled with the paste. Then, with an "ultrasonic scaler" (10,000 Hz) (Cavitron, Firma Dentsply) and with the water cooling switched off, the inlay is lowered into the filled cavity with slight pressure on the inlay surface. Due to the ultrasonic vibration the composite paste liquefies to such an extent that all excesses bulge out of the cementing gap and the inlay is pressed into the cavity until complete fitting is achieved. The excesses are thereafter removed with a probe and dental silk, this also being very simple due to the high viscosity of the paste. Thereafter, the cement is completely polymerised with all round exposure for 60 sec. with a commercially available dental radiation device (Elipar, ESPE). Then, the cement surface and the inlay are polished. No transitions can be seen and the inlay fits excellently.

If the method is carried out with the same material on the same inlay but without the action of ultrasonic vibration, the inlay cannot even be completely introduced into the cavity. Transitions from the tooth surface to the inlay are visible and can easily be detected with a probe.

Measurement of the Film Thickness 100 mg of the described composite are placed between a planar metal plate and a glass plate and uniformly distributed to a starting layer thickness of 500 $\mu$m. Thereafter, with the surface of the centre portion of the aforementioned ultrasonic scaler a pressure of 0.5 kP in each case is applied to the upper side of the glass plate. The pressure is left for 10 sec., firstly with the vibration switched on and then with no vibration. With the ultrasonic device switched on a film thickness of 10 μm is obtained. When the ultrasonic unit is not switched on the film thickness is 400 μm. Even by applying higher pressures (for example 10 kP) for longer times (for example 30 sec.) the film thickness does not go below 50 μm.

What we claim is:

1. A curable composition comprising ethylenically unsaturated monomers or polymers as a binder and 60–95% by weight of fillers of a mean grain size of <50 μm, said curable composition having a high viscosity, which renders said curable composition unworkable, and being liquefiable and workable by exposure to oscillation in a frequency range of 20 Hz to 20 MHz with an amplitude of 1 μm to 5 mm.

2. A curable composition according to claim 1, wherein said fillers and said binder are mixed by exposure to oscillation in said frequency range of 20 Hz to 20 MHz with said amplitude of 1 μm to 5 mm to form said curable composition.

3. A curable composition according to claim 1, wherein said curable composition is a dental filling composition.

4. A method for preparing a curable composition comprising ethylenically unsaturated monomers or polymers as a binder and 60–95% by weight of fillers of a mean grain size of <50 μm, said curable composition having a high viscosity, which renders said curable composition unworkable, and being liquefiable and workable by exposure to oscillation in a frequency range of 20 Hz to 20 MHz with an amplitude of 1 μm to 5 mm, said method comprising the step of:
mixing said fillers and said binder by exposure to oscillation in said frequency range of 20 Hz to 20 MHz with said amplitude of 1 μm to 5 mm.

5. A method according to claim 4, wherein said curable composition is a highly filled (meth)acrylate containing 60–95% by weight fillers.

6. A method of mixing multicomponent highly filled viscous composition, comprising the steps of:
mixing between two workpieces by shearing motions; and
setting into oscillation at least one of said workpieces in a frequency range of 20 Hz to 20 MHz with an amplitude of 1 μm to 5 mm.

7. A method according to claim 6, wherein said compositions comprise highly filled (meth) acrylates containing 60–95% by weight fillers.

8. A method according to claim 7, wherein said (meth)acrylates contain 70 to 95% by weight fillers.

9. A method according to claim 6, wherein said one workpiece is a vibrating spatula and the other one of said workpieces ia block.

10. A method according to claim 6, wherein said one workpiece is a vibrating spatula and the other one of said workpieces is a glass plate.

11. A method according to claim 6, wherein said one workpiece is a vibrating spoon-like body and the other one of said workpieces is a commercially available non-vibrating spatula.

12. A method of working a curable composition with a vibrating workpiece, said curable composition comprising ethylenically unsaturated monomers or polymers as a binder and 60–95% by weight of fillers of a mean grain size of <50 μm, said curable composition having a high viscosity, which renders said curable composition unworkable, and being liquefiable and workable by exposure to oscillation in a frequency range of 20 Hz to 20 MHz with an amplitude of 1 μm to 5 mm, said method comprising the step of:
setting into oscillation said vibrating workpiece in said frequency range of 20 Hz to 20 MHz with said amplitude of 1 μm to 5 mm.

13. A method of cementing inlays, onlays, and veneers with a highly filled dental filling composition in the form of a curable composition comprising ethylenically unsaturated monomers or polymers as a binder and 60–95% by weight of fillers of a mean grain size of <50 μm, said curable composition having a high viscosity, which renders said curable. composition unworkable, and being liquefiable and workable by exposure to oscillation in a frequency range of 20 Hz to 20 MHz with an amplitude of 1 μm to 5 mm, whereby said fillers and said binder are mixed by exposure to oscillation in said frequency range of 20 Hz to 20 MHz with said amplitude of 1 μm to 5 mm to form said curable composition, said method including the step of:
applying high-frequency vibrations to the inlays, onlays, veneers during cementing.

14. A method according to claim 13, wherein said high-frequency vibrations are generated by an ultrasonic device.

15. A method according to claim 14, wherein an intermediate layer is provided between said ultrasonic device and a part to be secured.

16. A method according to claim 13, wherein a frequency range of said high-frequency vibrations is 200 Hz to 1 MHz.

17. A method according to claim 16, wherein said frequency range has a lower limit of 10,000 Hz.

18. A method according to claim 13, wherein said fillers have a mean particle size of ≦5 μm and an upper grain limit of 25 μm.

19. A method according to claim 18, wherein 5–25% of said fillers have a mean particle size of 0.02–0.06 μm and 65–85% by weight of the fillers have a mean particle of 1–5 μm.

20. A method according to claim 13, wherein said dental filling composition is comprised of:
a) 60–95% by weight inorganic fillers;
b) 4–39.99% by weight ethylenically unsaturated polymerisable monomers and polymers;
c) 0.01–3% by weight photoinitiators;
d) optionally, activators, initiators for the initiation of redox polymerisation, pigments, X-ray opaque additives and thixotropy aids.

21. A method according to claim 20, wherein said dental filling composition is comprised of 70–90% by weight inorganic fillers, 9–29.9% by weight ethylenically unsaturated polymerisable monomers and polymers, and 0.1–2% by weight of photoinitiators.

22. A method according to claim 20, wherein said inorganic fillers have a mean particle size of ≦5 μm and an upper grain limit of 25 μm.

23. A method according to claim 22, wherein 5–25% of said inorganic fillers have a mean particle size of 0.02–0.06 μm and 65–85% by weight of the fillers have a mean particle size of 1–5 pm.

24. A method according to claim 20, wherein said ethylenically unsaturated polymerisable monomers and polymers are an acrylic acid ester of an alcohol having at least one OH-group.

25. A method according to claim 20, wherein said ethylenically unsaturated polymerisable monomers and polymers are a (meth)acrylic acid ester of an alcohol having at least one OH-group.

26. A method according to claim 13, wherein said dental filling composition is comprised of:
  a) 60-95% by weight inorganic fillers;
  b) 4-39.99% by weight ethylenically unsaturated polymerisable monomers;
  c) 0.01-3% by weight photoinitiators;
  d) optionally, activators, initiators for the initiation of redox polymerisation, pigments, X-ray opaque additives and thixotropy aids.

27. A method according to claim 26, wherein said dental filling composition is comprised of 70-90% by weight inorganic fillers 9-29.9% by weight ethylenically unsaturated polymerisable monomers, and 0.1-2% by weight of photoinitiators.

28. A method according to claim 26, wherein said inorganic fillers have a mean particle size of $\leq 5$ μm and an upper grain limit of 25 μm.

29. A method according to claim 28, wherein 5-25% of said inorganic fillers have a mean particle size of 0.02-0.06 μm and 65-85% by weight of the fillers have a mean particle size of 1-5 μm.

30. A method according to claim 26, wherein said ethylenically unsaturated polymerisable monomers are an acrylic acid ester of an alcohol having at least one OH-group.

31. A method according to claim 26, wherein said ethylenically unsaturated polymerisable monomers are a (meth)acrylic acid ester of an alcohol having at least one OH-group.

32. A method according to claim 13, wherein said dental filling composition is comprised of:
  a) 60-95% by weight inorganic fillers;
  b) 4-39.99% by weight ethylenically unsaturated polymerisable polymers:
  c) 0.01-3% by weight photoinitiators;
  d) optionally, activators, initiators for the initiation of redox polymerisation, pigments, X-ray opaque additives and thixotropy aids.

33. A method according to claim 32, wherein said dental filling composition is comprised of 70-90% by weight inorganic fillers, 9-29.9% by weight ethylenically unsaturated polymers, and 0.1-2% by weight of photoinitiators.

34. A method according to claim 32, wherein said inorganic fillers have a mean particle size of $<5$ μm and an upper grain limit of 25 μm.

35. A method according to claim 34, wherein 5-25% of said inorganic fillers have a mean particle size of 0.02-0.06 μm and 65-85% by weight of the fillers have a mean particle size of 1-5 pm.

36. A method according to claim 32, wherein said ethylenically unsaturated polymerisable polymers are an acrylic acid ester of an alcohol having at least one OH-group.

37. A method according to claim 32, wherein said ethylenically unsaturated polymerisable polymers are a (meth)acrylic acid ester of an alcohol having at least one OH-group.

* * * * *